(12) United States Patent
Emmert et al.

(10) Patent No.: US 9,581,578 B1
(45) Date of Patent: Feb. 28, 2017

(54) FULLY AUTOMATED SEQUENTIAL INJECTION ANALYSIS METHOD FOR PRECONCENTRATION OF HALOACETIC ACIDS IN DRINKING WATER SAMPLES

(71) Applicants: Gary L. Emmert, Collierville, TN (US); Paul S. Simone, Jr., Germantown, TN (US)

(72) Inventors: Gary L. Emmert, Collierville, TN (US); Paul S. Simone, Jr., Germantown, TN (US)

( * ) Notice: Subject to any disclaimer, the term of this patent is extended or adjusted under 35 U.S.C. 154(b) by 0 days.

(21) Appl. No.: 14/135,398

(22) Filed: Dec. 19, 2013

(51) Int. Cl.
G01N 30/84 (2006.01)
G01N 30/02 (2006.01)
G01N 33/18 (2006.01)
G01N 35/08 (2006.01)

(52) U.S. Cl.
CPC ......... *G01N 33/1826* (2013.01); *G01N 35/08* (2013.01); *G01N 2033/184* (2013.01)

(58) Field of Classification Search
CPC ........ G01N 30/84; G01N 30/02; G01N 30/00; G01N 30/96; G01N 2030/8435; G01N 2030/8429; Y10T 436/00; Y10T 436/11; Y10T 436/25; Y10T 436/2575

USPC ............... 436/52, 43; 73/61.56, 61.52, 61.43
See application file for complete search history.

(56) References Cited

U.S. PATENT DOCUMENTS

| 5,492,838 | A | * | 2/1996 | Pawliszyn | ............... | 436/178 |
| 6,025,202 | A | * | 2/2000 | Natan | ............... | B82Y 15/00 356/301 |
| 8,076,652 | B2 | * | 12/2011 | Emmert et al. | ............ | 250/458.1 |

* cited by examiner

*Primary Examiner* — Christine T Mui
(74) *Attorney, Agent, or Firm* — Wyatt, Tarrant & Combs, LLP; Stephen C. Hall

(57) ABSTRACT

The utilization of a specific preconcentration protocol within an automated, on-line drinking water analysis method to amplify detection levels of individual halo acetic acids is provided. The proposed sequential injection analysis procedures allow for measuring such levels in drinking water samples from remote locations with post-column reaction of ion chromatography (PCR-IC). The novel remote preconcentration method injects such known concentrations via a syringe at regular intervals in a manner to provide a baseline measurement that accords a reliable comparison with the unknown amounts present within the drinking water samples at issue. In such a manner, the on-line, remote system provides the necessary reliability for a water utility or like entity on which to base any further needed water treatment activities without having to perform such measurements in a distinct lab setting.

6 Claims, 7 Drawing Sheets

FULLY AUTOMATED SEQUENTIAL INJECTION ANALYSIS METHOD FOR PRECONCENTRATION OF HALOACETIC ACIDS IN DRINKING WATER SAMPLES

FIELD OF THE INVENTION

The present invention relates to the utilization of a specific preconcentration protocol within an automated, on-line drinking water analysis method to amplify detection levels of individual haloacetic acids. The proposed sequential injection analysis procedures allow for measuring such levels in drinking water samples from remote locations with post-column reaction of ion chromatography (PCR-IC). The novel remote preconcentration method injects such known concentrations via a syringe at regular intervals in a manner to provide a baseline measurement that accords a reliable comparison with the unknown amounts present within the drinking water samples at issue. In such a manner, the on-line, remote system provides the necessary reliability for a water utility or like entity on which to base any further needed water treatment activities without having to perform such measurements in a distinct lab setting.

BACKGROUND OF THE INVENTION

Drinking water has been, and continues to be, heavily treated for bacteria and other microscopic organisms that may cause infection in humans and other animals subsequent to consumption. In order to disinfect water supplies, halogenated materials have been introduced therein that have proven more than adequate for such a purpose. Unfortunately, although such halogenated compounds (chlorinated and chloraminated types, primarily) exhibit excellent disinfection capabilities, when present within aqueous environments containing organic compounds at certain pH levels these halogenated compounds may generate byproducts that may themselves create health concerns. The United States Environmental Protection Agency (USEPA) in fact regulates five specific types of haloacetic acids within drinking water, monochloroacetic acid, dichloroacetic acid, trichloroacetic acid, monobromoacetic acid, and dibromoacetic acid. Removal of such compounds from drinking water is not economically feasible thus, residual amounts may remain within treated water supplies that may require further removal processes to be undertaken. Of course, if the level of contamination is sufficiently low, initiation of such potentially expensive removal steps would be unwise from an economic perspective.

The USEPA currently has set a maximum contaminant level for the five haloacetic acids (collectively referred to as HAA5; four other haloacetic acids are currently not regulated by the USEPA, bromochloroacetic acid, bromodichloroacetic acid, dibromochloroacetic acid, and tribromoacetic acid; including these, the total haloacetic acid group is known as HAA9) at a total amount of 0.060 mg $L^{-1}$ and for the trihalomethanes at 0.080 mg $L^{-1}$. It is thus important to reliably analyze and measure the total amount of such contaminants in order to determine if removal or reduction is necessary.

The USEPA has instituted its own testing methods for such a purpose. One, known as EPA 552.2, involves the liquid-liquid extraction of haloacetic acids from water sources into methyl-t-butyl ether, followed by derivatization with acidic methanol to form the corresponding haloacetic acid methyl esters. Analysis by gas chromatography-electron capture detection provides reliable measurements of the haloacetic acid amounts present within the subject water supply. The other, USEPA 552.3, is a derivative of the first with optimizations of acidic methanol neutralization procedures for improvement in brominated trihalogenated haloacetic acid species. Both methods are generally robust and capable of analyzing diverse drinking water matrices for each HAA9 species with low method detection limit (MDL) values (<0.5 µg $L^{-1}$) and excellent accuracy and precision values. Such values are thus of great importance for any other type of drinking water analytical method in order to ensure exactness of results so the utility may properly respond to any measured levels that are unacceptably high. If the detection limits, however, are of an improper scale, the exact levels of such disinfection byproducts may be difficult to properly measure for such a purpose and the resultant drinking water samples may be considered acceptable when, in effect, such are outside the necessary parameters.

Unfortunately, these general processes have also been found to have numerous drawbacks, however. For instance, injection port temperature can affect debromination of certain haloacetic acid species (particularly tribrominated types) that may lead to under-representation of the amount of such contaminants present within the tested water source. Likewise, the water content of the methyl-t-butyl ether extract may decarboxylate the haloacetic acids, again leading to an under-reporting of the actual amounts present within the test sample. Furthermore, the involved processing needed to actually undergo such analysis makes an on-line protocol rather difficult to implement, particularly when hourly sampling is necessary. Other derivatization methods have been either followed or suggested for gas chromatography analyses of drinking water sources as well, including utilizing diazomethane, acidic ethanol, and aniline. Such reactant-based measurements, however, all suffer the same time and labor-intensive problems as with the two EPA test procedures noted above. As such, on-line analysis through these protocols are difficult, expensive, and labor intensive to implement.

Measurement at the source (i.e., within a water purification plant location) may be effective for system-wide average readings; however, in the large supplies of water at such locations, the chances of proper sampling to that effect may be suspect since the contaminants may be present in varied locations, rather than definitively mixed throughout the tested water supply itself. Additionally, testing may not uncover the actual level of residual haloacetic acid disinfection byproducts prior to the water supply being disbursed to distant dispense sites (transfer pipes, homes, schools, businesses, etc.). In any event, there is a relatively new regulation in place that requires utilities to provide evidence of compliance with haloacetic acid levels at multiple locations, rather than a straightforward system-wide average. Thus, since the above-described derivatization procedures with gas chromatography-electron capture detection analytical methods and purge and trap gas chromatography with either previously mentioned detector are not suitable for a uniform haloacetic acid measurement scheme, there is thus a drive to implement remote testing via real-time, on-line methods for water supply HAA5, and, more importantly, for HAA9 contaminant level measurements.

A variety of testing protocols have been suggested for water utility drinking water source analytical procedures. For instance, high performance liquid chromatography, utilizing electrospray ionization-mass spectrometry or ultraviolet absorbance as the detector, has been attempted, as well as ion chromatography, with membrane-suppressed conductivity detection or, as well, ultraviolet absorbance detection. Other attempts with inductively coupled plasma-mass spectrometry and electrospray ionization-mass spectrometry coupled with ion chromatography have been followed as well for this same purpose. The detection level can be as low as 0.5 to less than 10 μg $L^{-1}$ for HAA9 species, but only subsequent to sample preparations. The sensitivity and selectivity of ion chromatography and high performance liquid chromatography methods are easily sacrificed without the cumbersome preparations in place, therefore requiring operator intervention during analysis. Again, as with the USEPA methods, these issues invariably lead to serious drawbacks when on-line implementation is necessary. Attempts at implementing these measuring schemes in such a desirable on-line, remote test procedure have basically failed.

However, such a desirable on-line procedure has been achieved, to a certain extent, for the determination of both the amount and separate identification of each haloacetic acid species (within a certain degree of reliability, such a unique process allows for a rough determination in an on-line setting of the amount of each separate species present within the tested water source). Unfortunately, however, such a new test protocol does not provide a specific enough measurable result to match the necessarily effective MDL results provided by both USEPA 552.2 and 552.3 standards (which are roughly a degree of magnitude more effective). Since any measurements made along a water line must provide extremely reliable results in this manner, particularly at any point along such a line, there remains a noticeable need to increase the degree of measurement reliability for an on-line, remote system. Again, since the USEPA test standards are not effective in such settings, such a need is amplified as proper HAA5 (or HAA9) measurements are required to be as specific (and thus as reliable) to the same levels as for USEPA 552.3, at least, along the entirety of a water line to be acceptable. With the increase in water needs around the country (if not the planet), and the requirement that such water sources not only exhibit proper levels of microbe activity (essentially, or, at least, desirably, none), and thus are subject to chlorination (or chloramination) to a large degree, the need to provide a more reliable testing measure for such chlorination byproducts within a drinking water line is evident.

As well, the ability to provide such test results in an on-line, remote setting to the degree of magnitude that mirrors those obtained through the USEPA test standards should be time-effective and involve the utilization of suitable (and reliable) reagents to generate such reliable measurements. It is important to realize, too, that the USEPA standards are tedious, time consuming, and require a skillful hand for successful analysis. For instance, these procedures require over 20 consecutive steps for sample preparation, followed by a 40 minute analysis time using gas chromatography with electron capture detection (GC-ECD). Both USEPA methods excel at parallel, grab-sample analysis, but primarily where turnaround times of 1 to 2 days are acceptable. The current regulations, though, as alluded to above, require greater efficiencies such that a water utility needs to know the specific levels of HAA activity is along a water source line as soon as possible in order to effectuate the necessary additions of reagents therein to combat such carcinogenic materials immediately. As such, the USEPA tests are simply improper (and inefficient) for on-line, real-time monitoring and optimization where such immediate turn-around for concentration data is required.

The prior on-line systems that have been developed to compete with the USEPA standards utilize a post-column reaction-ion chromatography platform (PCR-IC) with two different forms of selectivity for the HAA9 species: 1) separation using an ion chromatography column and 2) reaction with nicotinamide in basic solution as post-column reagent to produce a fluorescent product. The problem with the original protocol, unfortunately, was that bromochloroacetic acid interfered with dichloro- and dibromoacetic acid quantifications. Despite this problematic limitation, it was determined that fluorescence detection provided a much improved detection protocol in comparison with ultraviolet absorbance and mass spectrometry possibilities. Thus, although such a fluorescence method of detection, coupled with the post-column reaction (again with nicotinamide reagent) and ion chromatography, exhibited the best results in terms of an on-line test method for HAA5 drinking water contaminant measurement levels, there remained a definite need for improvements in total haloacetic acid measurements and identifications within such test samples. Since then, this PCR-IC method for HAAs has been updated for determination of HAA9 species and inclusion of an on-line, internal standard calibration protocol using 2-bromobutanoic acid (2-BBA). This PCR-IC method is an efficient analyzer for on-line, real-time monitoring of the HAA9 species, and reports concentration data immediately after analysis. This protocol also does not require manual sample handling or preparation steps prior to analysis, and uses commercial, off-the-shelf components. As well, such an alternative has permitted compensation for both random and systematic errors, accounts for any signal fluctuations, and drastic reductions in calibration time.

Such a PCR-IC instrument has been extensively compared with the USEPA 552.3 standard, based particularly on MDL, accuracy, precision, and side-by-side comparison studies in real-world drinking water samples. The MDL values for the individual HAA9 species for the PCR-IC range from 1-5 μg $L^{-1}$ and the USEPA MDLs range from 0.04 to 0.4 μg $L^{-1}$, both with acceptable accuracy and precision as defined by the USEPA. The MDL values for the PCR-IC are generally an order of magnitude larger than the USEPA MDL values, but despite this difference, the bias between the two methods is acceptable in drinking water samples, with Total HAA9 concentrations ranging from 5 μg $L^{-1}$ up to 50 μg $L^{-1}$. The bias of the individual HAA9 species was found to be within a factor of 1-1.5 of the respective MDL, thus bias values for DCAA are expected to be highest since it has the highest MDL of the HAA9 species.

The empirical relationship between bias and MDL indicates that improving the MDL values of the PCR-IC analyzer will also improve the bias between PCR-IC and the USEPA 552.3 analysis. Unfortunately, such improvements have proven difficult to achieve, particularly in a manner that allows water utilities to completely (or significantly) supplant the utilization of USEPA standards as the basis of HAA measurements within drinking water supplies. Again, the ability to provide reliable, effective, and timely MDL levels for drinking water HAA concentrations, in this respect, would be highly desirable within this industry.

Of possibly even greater interest, however, is the capability of any such system to provide reliable testing results at effective time intervals. Past measuring techniques have proven effective on monthly or quarterly schedules; desired timeframes, however, as noted above, are hourly, at least, instead. The past analytical procedures discussed above, are rather difficult to employ at remote locations to begin with; to attempt testing every hour further exacerbates an already cumbersome procedure. On-line monitoring, though highly prized in the drinking water industry, has thus proven difficult to employ. Even with mobile methods in use, bench-top scale instruments have been necessary, rather than portable devices for such applications. Additionally, the reliability of any such on-line monitoring system has been highly suspect due to fluctuations in readings as calibration for short-term measuring intervals has not been easily incorporated therein, let alone actually followed.

To compound the difficulties associated with on-line monitoring systems of this type, the reliability of measurement and analysis of water samples is based upon the capability of the overall system to provide reproducible results at different times. With a standard sample provided for rather long periods of time until a new sample may be introduced within the remote system, the possibility that the standard has been altered through temperature fluctuations over time, or growth or production of undesirable organisms or chemical species therein during storage may cause problems ultimately in the resultant measurements.

There thus exists a need to provide an effective remote calibration system in order to alleviate such potential analytical disparities. To date, the best on-line, remote systems employed for such drinking water analysis at hourly intervals appear to lack the necessary degree of concentration measurements set forth by the USEPA protocols. Even with a calibrated procedure that allows for more reliable measures at different time intervals, the primary deficiency lies in the exactness of the actual measurement levels. As noted above, the MDL recordations for USEPA tests are a full magnitude below that for these prior PCR-IC test procedures, both with and without calibration steps present. Thus, again, there still remains a need to provide such an effective on-line, remote drinking water analysis process, but with measurement levels on par with USEPA results. Such a continuous system would basically involve testing procedures that are automatically undertaken remotely in regular intervals, whether by the hour, minute, day, etc. The ability to undertake remote testing and analysis permits on-line and real-time quantification and/or qualification of potential contaminants (i.e., total haloacetic acid species) with little human involvement in the overall testing procedures thus provides significant efficiencies to such overall water sample testing capabilities. In order to provide reliable data in such remote locations, there is an expressed need to provide such effective MDL measurement results within the overall testing system in order to ensure the user is provided the most exact measurements on demand at any point of the subject water line, and when the contaminants themselves are most likely present at rather low concentrations. The capability of not only providing an on-line method for such contaminant analysis, but, as well, an overall water analysis system that functions remotely, too, would thus permit the greatest level of reliability possible on which a water utility or other like entity would base its water treatment activities, particularly when based upon water samples located within transfer lines, and not solely present in a laboratory. To date, although prior water analysis methods have been attained and proposed for on-line, remote analytical purposes, the ability to provide remote water testing protocols that render highly reliable and exact measurements without human interaction or like involvement has not been provided the pertinent industries.

ADVANTAGES AND SUMMARY OF THE INVENTION

It is an advantage of the present invention to provide a reliable on-line drinking water analytical protocol for determining total haloacetic acid concentrations at roughly the same magnitude as provided by USEPA 522.3. It is an additional advantage of the invention to provide such reliable data at any location along a drinking water supply line without need for operator involvement by implementing automatic operation, calibration, and a sequential injection analysis component including a solid phase extraction assembly providing preconcentrations of haloacetic acids. Yet another advantage is the ability to deliver such effective measurements in an on-line setting, thereby permitting generation of sufficiently reliable data for an operator to determine if further actions are necessary to correct for high levels of halogenated contaminants in the tested water supply.

Accordingly, the invention encompasses a fully automated method of analyzing drinking water samples in an on-line procedure and at a remote location along a drinking water supply line, said method including the identification and detection of concentration of haloacetic acid disinfection byproducts therein said drinking water sample, said method comprising:

a) providing at least one drinking water sample stream that has been disinfected with chlorinated or chloraminated disinfectants;

b) providing a sequential injection analysis module, wherein said module includes a solid phase extraction component (such as a cartridge including therein a suitable polymeric resin, such as LiChrolut EN, as one non-limiting example); a chemical reagent pump; a valve to permit separate delivery of water and chemical reagents to said solid phase extraction component, wherein said reagents include a solid phase extraction component conditioning reagent, an acidic reagent, and a basic reagent; and a separate drinking water sample stream and acid delivery pump to deliver acidified drinking water samples to said solid phase extraction component;

c) conditioning said solid phase extraction component through introduction therein with said solid phase extraction component conditioning reagent (such as methanol, as one example);

d) feeding said drinking water sample stream through said drinking water sample stream delivery pump into said solid phase extraction component with said acidic reagent from said chemical reagent pump (preferably dilute sulfuric acid, as one non-limiting example) and through said valve, thereby removing at least some of the haloacetic acids from said drinking water stream and forming an acidified preconcentrate formulation including at least one haloacetic acid bound to said solid phase extraction component (which is preferably bound on the surface of said solid phase extraction component)(and, alternatively, flushing said solid phase extraction component with water through said valve);

e) feeding said basic reagent through said solid phase extraction component to elute said acidified preconcentrate formulation of step "d" from said solid phase extraction component;

f) feeding the eluted preconcentrate formulation of step "e" through a PCR-IC instrument;

g) feeding said resultant preconcentrate formulation of step "f" through a guard column and an anion exchange column to provide separated haloacetic acid species streams;

h) mixing said separated haloacetic acid species streams from step "g" with a dilute base and a fluorescing compound to form a separate fluorescing haloacetic acid species streams therein; and i) transporting said separate fluorescing haloacetic acid species streams of step "h" to a fluorescence detector to determine the concentration of total haloacetic acids within all such fluorescing haloacetic acid species streams through fluorescence detection.

This method also encompasses a two-component analytical instrument including:
i) a sequential injection analytical module and
ii) a PCR-IC device;

wherein said sequential injection analytical module includes a solid phase extraction component, two separate pumps, and a multi-port valve allowing for alternating streams to lead from one of said separate pumps to said solid phase extraction component, wherein said other separate pump leads to said solid phase extraction component, and wherein said solid phase extraction component leads to said PCR-IC device.

A sequential injection analysis (SIA) module has thus been developed for automated preconcentration of haloacetic acids (HAAs) prior to analysis by post-column reaction-ion chromatography (PCR-IC) with nicotinamide fluorescence. The preconcentration is achieved by solid phase extraction (SPE) with, for example but not limited to, LiChrolut EN cartridges (a PS-DVB resin designed for environmental analysis). Optimization of method parameters is described and detailed method detection limit (MDL), accuracy, precision, and linearity studies are presented. MDL values for the individual HAA9 species are at or below 1.0 µg $L^{-1}$. Side-by-side comparison studies of HAAs analysis in real-world drinking water samples are presented that compare the optimized method and USEPA Method 552.3. Trace levels of HAAs detected in the samples are reported and the bias values calculated between the two methods are acceptable overall.

Prior analytical methods have permitted implementation of remote automatic testing procedures and instrumentation along any location of a drinking water supply line. As noted above, these previous analytical approaches suffered from a rather high magnitude of measurement results such that the reliability of such procedures may not be acceptable within USEPA requirements. To the contrary, the inventive method has provided a comparable test method in terms of such reliability levels, but coupled with the capability of utilization along any point of a drinking water line.

This significant improvement is based upon an increase in the amount of HAAs injected within the subject PCR-IC analyzer. Such a desire to measure trace levels of HAAs (levels which are typically hard to detect utilizing past on-line, remote drinking water test procedures) in drinking water has required some manner led to significant research in preconcentration approaches for HAAs including: liquid-liquid extraction used in USEPA 552.2 and 552.3; liquid-solid ion-exchange; and solid phase extraction (SPE) techniques have been reported using activated carbon and polymeric resins such as LiChrolut EN.

SPE techniques are particularly attractive for automation due to the relative simplicity of the extraction and elution of the HAAs from the matrix, compared to automation of liquid-liquid extraction techniques. Preconcentration of HAAs using SPE follows four basic steps: (1) conditioning the cartridge (2) loading the acidified sample (3) rinsing the cartridge and (4) eluting the sample. The sample is acidified to protonate the HAAs such that hydrophobic interactions between the HAAs and resin can occur. The LiChrolut EN resin is one highly effective, non-limiting, candidate for such an automated HAA preconcentration process because the polymeric resin is well suited for environmental matrices, has a large pH stability range (pH 1-13), and can tolerate the pH extremes of sample loading and elution.

The SPE preconcentration techniques previously disclosed have concerned limited method steps, basically employing manual or semi-automated analysis, with human interaction (analysis) required to handle the subject samples at each process step. Adapting the HAAs preconcentration steps using traditional flow injection analysis (FIA) techniques (which have been undertaken with prior on-line drinking water analysis methods in the past) requires complex valving due to the discontinuous steps involved. However, and to the contrary, it has been determined that sequential injection analysis (SIA) provides excellent results because it uses discontinuous, bidirectional flow as opposed to the continuous, unidirectional flow used in FIA. Additionally, certain commercial SIA instruments typically include a stream-selection valve, a pump, a reactor, and a detector, all controlled by a single dedicated software source. Thus, SIA retains the advantages of FIA for fluid handling including highly reproducible flow rates and timing, while providing distinct improvements in comparison thereto through the reduction of necessary sample and reagent usage. Although there have been discussions of SIA applications in drinking water analysis in the past, such disclosures have been limited in scope to water sample analysis, multiparametric determinations, in-line treatments, separation/preconcentration issues, metals determination, non-metals determination, and off-line pre-treatment. No disclosures, however, have been provided that utilizes any SIA platform in relation to the analysis of drinking water chlorination (or chloramination) byproducts, notably HAAs (nor trihalomethanes, another class of undesirable, carcinogenic byproducts, either).

Thus, the inventive system is directed to, as noted above, a fully-automated procedure for preconcentration and analysis of HAAs in drinking water by using SIA and PCR-IC. Such an inventive method greatly improves the MDL values and performance of the PCR-IC analyzer with a modest increase in analysis time. Through a great deal of repetitive analysis, however, optimization of the analytical parameters for each step in the preconcentration method were achieved and are presented in greater detail below (based primarily upon the % recovery of the HAA9 species from an on-line drinking water sample). After optimization, detailed MDL, accuracy, precision, and linearity studies were conducted, followed by side-by-side, real-world sample analyses comparing the SIA-PCR-IC to USEPA 552.3 to show the beneficial results of implementing this inventive procedure in an on-line, remote drinking water analysis process.

DESCRIPTION OF THE PREFERRED EMBODIMENTS AND DRAWINGS

All the features of this invention and its preferred embodiments will be described in full detail in connection with the following illustrative, but not limiting, drawings and examples.

Instrumentation and Initial Tests

The SIA-PCR-IC instrument operates as two, semi-independent systems. The SIA module conducts all sample preparation, preconcentration, and elution of the HAAs from the LiChrolut EN cartridge into the sample loop on the PCR-IC injection valve. After injection, the PCR-IC system performs the separation of the HAA9 species, reaction with nicotinamide, and fluorescence detection (excitation 365 nm, emission 455 nm).

Figure 1:
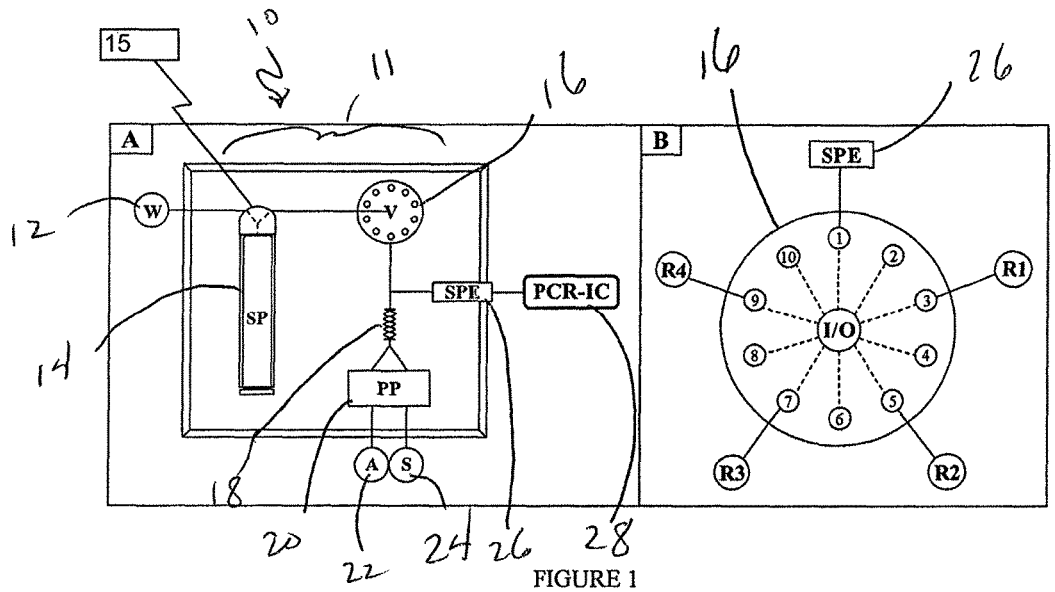
FIG. 1A is a Flow diagram of the SIA module used for automation of the preconcentration method.
FIG. 1B depicts a closer view of a 10-port valve utilized within the SIA module of FIG. 1A.

FIG. 1A shows a Flow diagram of the entire on-line analyzer instrument 10 including the sequential injection analysis module 11. The module 11 includes at least one syringe pump (preferably, but not limited to, a 10 mL pump) 14 with a 2-way valve 15 attached to permit control of chemical reagents feeding though a 10-port stream selector valve 16 or an external waste reservoir 12. Also within the module 10 is an additional independent pump 20 (here a peristaltic pump, but two syringe pumps are acceptable, as an alternate example) and a mixing coil 18 feeding into a solid phase extraction cartridge 26. Feeding into the peristaltic pump 20 are streams of sulfuric acid 22 and water standards or samples 24. The solid phase extraction cartridge leads to the post-column reaction-ion chromatography instrument 28. FIG. 1B thus shows the 10-port stream selector valve 16 in closer view with each of the ports 1-10 shown in radial fashion from a center point of the round valve. Further depicted are specific ports R1-R4 in terms of the potential embodiments of the valve in relation to the reagents introduced. Ultimately, as in FIG. 1A, this valve transfers chemical reagents to the solid phase extraction cartridge 26. Thus, for this potentially preferred embodiment, R1 is methanol (to condition the solid phase extraction cartridge), R2 is sulfuric acid (in dilute form, as one possible example, to acidify the drinking water sample for haloacetic separation and binding to the resin), R3 is reagent water (to flush the cartridge), and R4 is NaOH (in dilute form as one example, again, to elute the haloacetic acids bound to the resin). The indication I/O within the valve 16, is present to show the line into and out of the valve connects to the syringe pump (15 of FIG. 1A).

Figure 2:
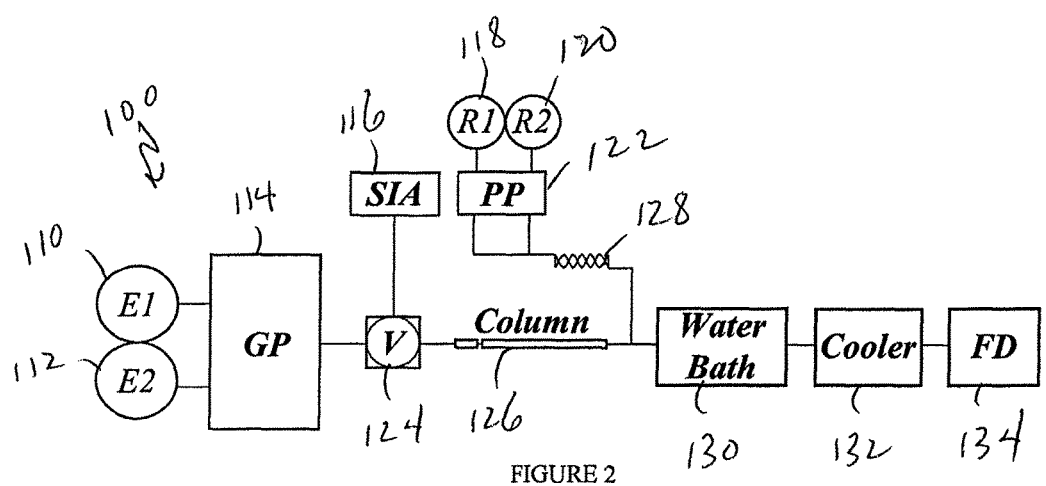
FIG. 2 is a block diagram of the PCR-IC instrument using nicotinamide fluorescence with SIA preconcentration.

FIG. 2 is thus a block diagram of the entire PCR-IC instrument 100 using nicotinamide fluorescence with SIA preconcentration. A first eluent (here, preferably 200 mM KOH eluent) 110 and a second eluent (reagent water) 112 feed into a gradient pump 114 (though both eluents can be altered to suitably affect separation of the HAAs) which leads into a multi-port sample injection valve 124 (such as a 6-port injection valve or possibly a 10-port injection valve). The sequential Injection Analysis preconcentration module 116 (as more succinctly described in FIG. 1A) also feeds into the same multi-port valve 124. The valve 124 thus allows for injection of the portion of the preconcentrate from the SIA module 116 that contains the highest HAA concentrations into a continuously flowing stream of mixed eluent from first and/or second eluent 110, 112 to feed into the column (or columns; preferably this includes guard and analytical anion-exchange columns) 126. Past the column is introduced a stream of 2.0 M KOH reagent 118 and 3.07 M nicotinamide reagent 120, through a peristaltic pump 122 and a mixing coil 128. This mixed stream then feeds into a 98° C. water bath containing a reaction coil 130 and then a Peltier cooler 132 (or any equivalent component or ice bath) to reduce the temperature so that the resultant samples may then be transferred to a fluorescence detector 134 to analyze the concentration of nicotinamide fluorescing samples therein.

The purity of all chemicals used was higher than 97%, except for 85% reagent grade potassium hydroxide (KOH). All standards, reagents, and eluents were prepared in reagent grade water with a resistivity of 18.2 MΩ·cm (ThermoScientic Barnstead E-pure). Glassware was cleaned with concentrated detergent and rinsed thoroughly with reagent water. MCAA, MBAA, DCAA, BCAA, DBAA, TCAA, BDCAA, DBCAA, TBAA, and nicotinamide were obtained from Sigma-Aldrich. KOH, NaOH, sulfuric acid ($H_2SO_4$), methanol, methyl tert-butyl ether (MTBE), and 2-bromobutanoic acid (2-BBA) were obtained from Fisher Scientific.

A 1000 mg $L^{-1}$ HAA9 stock standard solution was prepared by adding 25 mg of each HAA9 species to a 25.00 mL volumetric flask and diluting with MTBE. A 10 mg $mL^{-1}$ IS stock standard solution was prepared by diluting 0.100 g of 2-BBA to 10.00 mL of MTBE. These stock solutions were diluted accordingly with reagent water daily and subsequently used for optimization and calibration studies. The post-column reagents were prepared by dissolving 75.0 g nicotinamide in 140 mL reagent water for a total volume of 200 mL (3.07 M), and 25.5 g KOH dissolved in 200 mL reagent water (2.0 M). The reagent water used for eluent preparation was degassed using nitrogen; the 200 mM KOH eluent was prepared by dissolving 12.75 g in 1.0 L of degassed reagent water. The sulfuric acid preconcentration reagent was prepared by diluting concentrated $H_2SO_4$ sulfuric acid into reagent water as needed. A 1.0 M NaOH solution was prepared by weighing 40.0 g of NaOH into 1.00 L of reagent water and diluted appropriately to produce the various NaOH concentrations used in the optimization studies.

These reagents were then utilized within the instruments outlined above and provided in greater detail below to determine haloacetic acid concentrations within disinfected water supplies along a sourcing line. Such potentially preferred embodiments of these methods are presented as follows:

The SIA module (FIAlab Instruments, Bellevue, Wash., USA) (11 of FIG. 1A) was used to automate the preconcentration steps for HAAs. The SIA module 11 consisted of a multiposition, 10-port stream selection valve 16 from VICI (Houston, Tex., USA) connected to a four channel peristaltic pump 20 and 10-mL, programmable syringe pump 14. The SIA module 11 was computer controlled using FIAlab for Windows 5.0 software (not illustrated). The syringe pump 14 was used to aspirate a reagent (methanol, acid, base, or reagent water) from the stream selector valve 16 (presented in greater detail, again, in FIG. 1B), and then dispense an exact amount through the SPE cartridge 26. The peristaltic pump 20 was used to acidify a standard or sample and then flow through the SPE cartridge 26 for extraction and preconcentration. Both the syringe pump 14 and peristaltic pump 20 were connected to the SPE cartridge 26 through a tee fitting. When SPE cartridge 26 conditioning was done with the syringe pump 14, the peristaltic pump 20 was off and blocked, thus flow was through the SPE cartridge 26. The reverse is true when sample acidification and loading on the SPE cartridge 26 is conducted with the peristaltic pump 20. The preconcentrated HAA sample is eluted into a 2-mL sample injection loop (not illustrated) of the PCR-IC system 28 and injected for analysis. The SIA instrument 10 was interfaced with PeakSimple software (not illustrated) via contact closure which is used to remote start the PCR-IC analyzer 28. The SPE cartridge 26 was prepared by filling an empty 4×50 mm guard column (126 of FIG. 2) with 200 mg of LiChrolut EN resin (Merck-Millipore, Darmstadt, Germany).

The optimized preconcentration procedure used the syringe pump 14 to deliver reagents for the conditioning, rinsing, and elution steps while the peristaltic pump 20 was used for the loading step. A sample volume of 50 mL was loaded and eluted into exactly 2 mL (PCR-IC sample loop), giving a theoretical preconcentration factor of 25. Each of the steps in the preconcentration procedure was automated using the FIAlab SIA module and software. For the conditioning step, the selection valve was switched to port 3 (R1) and the syringe pump filled with methanol; the valve was then switched to port 1 (SPE) and the syringe pump dispensed 3 mL of methanol at 2 mL min$^{-1}$. Next, 50 mL of sample was acidified with 1.0 M $H_2SO_4$ to a pH 1.2 using two channels of the peristaltic pump, and flowed onto the SPE cartridge (this step can also be accomplished with two syringe pumps or any set of devices affects flow of liquid). The sample and $H_2SO_4$ were mixed at rates of 2.0 mL min$^{-1}$ and 0.5 mL min$^{-1}$, respectively. The stream selection valve was switched to port 7 (R3) and the syringe pump filled with reagent water. Then, the selection valve was switched to port 1 (SPE) and the syringe pump dispensed 1 mL at 2 mL min$^{-1}$ to rinse the SPE cartridge. Finally, the valve was switched to port 9 (R4) and the syringe pump filled with 10 mM NaOH. The valve then switched to port 1 (SPE) and the syringe pump dispensed 3 mL at 0.5 mL min$^{-1}$, eluting the preconcentrated sample directly into the 2 mL sample loop (not illustrated) of the PCR-IC system 28 and followed by injection for analysis. After dispensing each reagent, the syringe pump 14 was first rinsed twice with 1 mL of reagent water followed by rinsing twice with 1 mL of the next reagent before the fill-and-dispense steps of the next reagent.

The SIA-PCR-IC system components are, as noted above, illustrated in FIG. 2. A Dionex GP-50 (Sunnyvale, Calif., USA) gradient pump 114 was used to separate the HAA9 species using a binary gradient with 200 mM KOH and reagent water. The 2 mL of eluate from the SIA preconcentration system 116 was injected onto the PCR-IC system using a six port, high pressure sample injection valve 124 (VICI; Houston, Tex., USA). The separation was performed on a Dionex AG-18 (50×4.6 mm) and AS-18 (250×4.6 mm) guard and analytical column 126, respectively. Post-column reagent flow was accomplished using a FIAlab 2000 (Bellevue, Wash., USA), four channel peristaltic pump 122. The nicotinamide and KOH post column reagents were premixed using a knitted open tubular reaction coil 128 (KOT; 1 m×0.75 mm I.D.; BiotechAB, Sweden) followed by mixing with the effluent of the separation column 126 using 40 m of KOT (four, 10 m×0.75 mm I.D.) heated to 98° C. in a Fisher Scientific 5 L water bath 130 (Pittsburgh, Pa., USA). The reaction mixture was cooled with a Peltier device 132 set to ~4° C. prior to fluorescence detection using a Shimadzu RF-551 134 (excitation 365 nm, emission 455 nm; Kyoto, Japan). The gradient pump 114, valve 124, peristaltic pump 122, and detector 134 were all automated and controlled by PeakSimple software (SRI Instruments)(not illustrated).

The gradient pump 114 was set at a constant flow rate of 1 mL min$^{-1}$. The gradient program for separation and elution of HAA9 was as follows: initial conditions (1% of 200 mM KOH and 99% of reagent water) were held for 1 minute; from 1 to 2 minutes, the percentage of KOH was increased to 3% and was held for 2 minutes; from 4 to 10 minutes, it increased to 4% and was held for 3 minutes; from 13 to 15 minutes, it increased to 7%; from 15 to 20 minutes, it increased to 15%; from 20 to 23 minutes, it increased to 18%; from 23 to 27 minutes, it increased to 20%; from 27 to 31 minutes, it increased to 55%; from 31 to 38 minutes, it increased to 90%; from 38 to 47 minutes, it increased to 96%; and from 47 to 52 minutes, it decreased back to the initial conditions of 1%. The separation program detailed here is just an example. Any gradient program which affects separation is acceptable.

Figure 3:
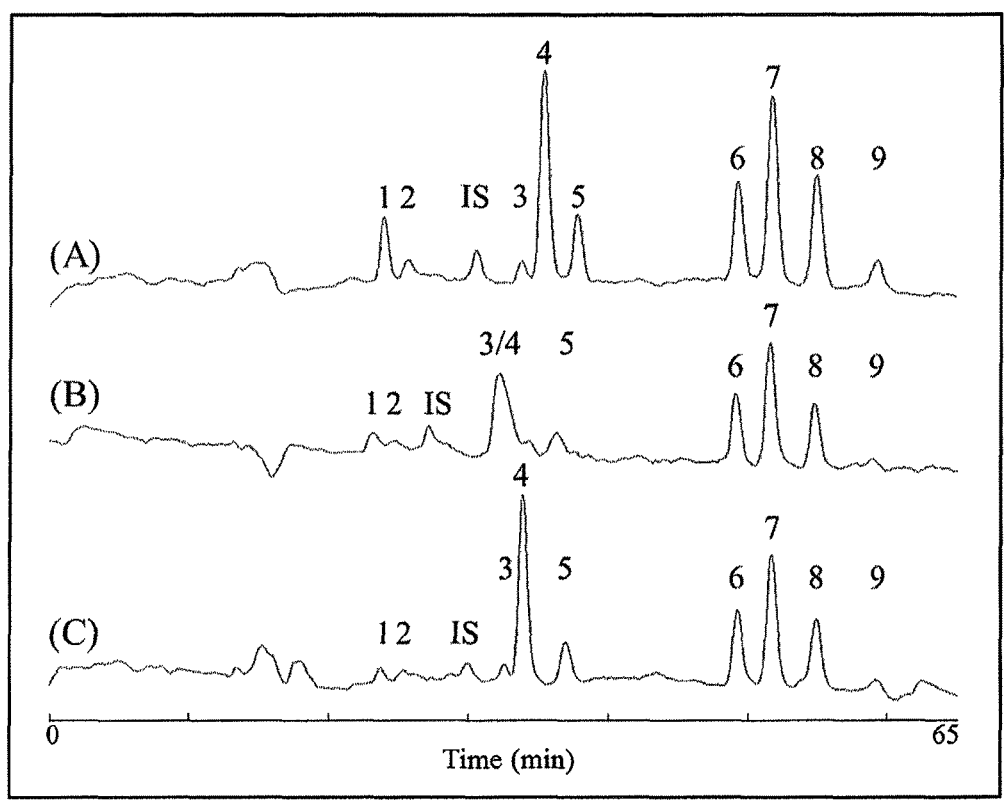
FIG. 3 shows chromatograms comparing preliminary trials using the automated SIA preconcentration method prior to analysis by PCR-IC with nicotinamide fluorescence.

FIG. 3 thus shows chromatograms comparing preliminary trials using the automated SIA preconcentration method prior to analysis by PCR-IC with nicotinamide fluorescence. The provided chromatograms show results for (A) 50 μg L$^{-1}$ HAA9 standard (no preconcentration); (B) 2 μg L$^{-1}$ HAA9 standard preconcentrated without the dilute sulfuric acid step; and (C) 2 μg L$^{-1}$ HAA9 standard preconcentrated with the dilute sulfuric acid step included in the cartridge conditioning. These chromatograms are in relation to the following legend to describe the test subjects: 1—MCAA; 2—MBAA; IS—Internal standard (2-BBA); 3—DCAA; 4—BCAA; 5—DBAA; 6—TCAA; 7—BDCAA; 8—DBCAA; 9—TBAA.

Preliminary studies prior to optimization determined that only the methanol conditioning step was necessary. Rinsing the SPE cartridge with 0.2 M sulfuric acid after the methanol step resulted in poor chromatographic resolution of the dihalogenated HAAs species (see B of FIG. 3). Without this first conditioning step, the resolution was comparable to the typical chromatograms produced by the PCR-IC without preconcentration (A and C of FIG. 3).

The methanol conditioning step involved delivery of a 3 mL aliquot of methanol through the SPE cartridge 26 through activation of the syringe pump 14. An optimization of the delivery flow rate was conducted from 1 to 4 mL min$^{-1}$. The results of the study found that the % Recovery of individual and Total HAA9 species spanned no more than 10% except MBAA which increased of 21% from 1 to 2 mL min$^{-1}$, then decreased from 2 to 4 mL min$^{-1}$. The optimal flow rate of the methanol conditioning step was determined to be 2 mL min$^{-1}$ with average % Recoveries results as follows: 20±0% for MCAA, 42±8% for MBAA, 51±1% for DCAA, 92±1% for BCAA, 95±3% for DBAA, 72±4% for TCAA, 70±0% for BDCAA, 55±0% for DBCAA, 30±9% for TBAA, and 67±1% for the Total HAA9.

Subsequent to this initial determination, more detailed refinement was sought for the overall method.

Optimization of Method Parameters

Thus, prior to detailed MDL, accuracy, precision, linearity, and real-world sample analyses, each parameter of the preconcentration method was optimized, including the SIA reagent and sample flow rates, sample pH, eluent concentration, and elution profiles. Each optimization study was conducted by consecutive, duplicate analyses and conditions were changed accordingly via software. For each condition, a 50 μg L$^{-1}$ HAA9 standard was analyzed first followed by a preconcentrated 2 μg L$^{-1}$ HAA9 standard. The % Recovery was calculated by dividing the peak areas of a preconcentrated 2 μg L$^{-1}$ HAA9 standard by the peak areas of a 50 μg L$^{-1}$ HAA9 standard and multiplying by 100. Thus, 100% Recovery of a 2 μg L$^{-1}$ HAA9 standard after preconcentration should produce peak areas equal to a 50 μg HAA9 standard (without preconcentration). Finally, a plot of the % recovery of the individual HAA9 species was constructed and inspected, and the optimal value was then chosen based on % Recovery of a majority of individual HAA9 species. However, if a plot showed no clear trend, then the optimal value was based on % Recovery of DCAA because it has the lowest PCR-IC fluorescent intensity and is the most common HAA9 species present in drinking water.

Figure 4:
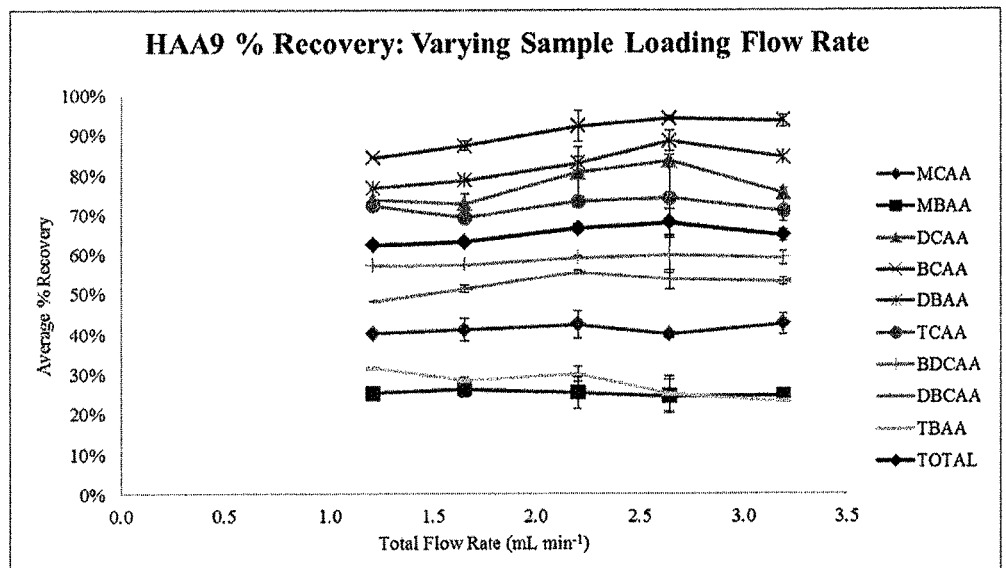
FIG. 4 is an optimization plot for sample loading flow rates of the inventive method.

The flow rates for sample loading and elution are expected to have more effect on % Recovery than the flow rate of the methanol conditioning step, since both act on the sample directly. The total loading flow rate was varied over the range of approximately 1.2 to 3.2 mL min$^{-1}$ in 0.5 mL increments (FIG. 4). In these studies, the ratio of sample to acid flow was 10:1 (e.g. sample was 1.0 mL min$^{-1}$ and acid was 0.1 mL min$^{-1}$). The % Recovery of the HAA9 species increased slightly with increasing flow rate and ranged from 2% increase for MBAA up to 11% for DBAA, while the average Total HAA9% Recovery increased by 5%. The average % Recoveries at the optimum 2.2 mL min$^{-1}$ total flow were as follows: 42±3% for MCAA, 25±4% for MBAA, 80±6% for DCAA, 92±4% for BCAA, 83±2% for DBAA, 73±1% for TCAA, 59±0% for BDCAA, 55±1% for DBCAA, 30±2% for TBAA, and 67±1% for the TOTAL. The optimal, sample loading total flow rate is observed at 2.6 mL min$^{-1}$ with six of the nine HAA species exhibiting a maximum % recovery.

FIG. 4 shows the optimization plot for sample loading flow rates between 1.1 and 3.3 mL min$^{-1}$. The results indicate the effectiveness of increased loading flow rate for such measurements.

Elution flow rate was then improved upon. Notably, the protonated HAAs are adsorbed onto the SPE resin via hydrophobic interactions. The NaOH reagent deprotonates and ionizes the HAAs and elutes them from the cartridge. For the flow rate optimization, a concentration of 0.01 M was used as a starting point. A four point, preliminary survey from 0.5 to 2.0 mL min$^{-1}$ found the optimal range to lie between 0.25 and 1.0 mL min$^{-1}$. A more detailed study was conducted between 0.3 and 1.0 mL min$^{-1}$ (FIG. 5) and determined that the overall best elution rate was 0.5 mL min$^{-1}$. The average % Recoveries resulting from the optimized condition was 38±1% for MCAA, 27±8% for MBAA, 78±11% for DCAA, 92±7% for BCAA, 90±4% for DBAA, 74±8% for TCAA, 70±3% for BDCAA, 55±2% for DBCAA, 40±6% for TBAA, and 70±4% for the TOTAL.

After loading the sample onto the cartridge, a reagent water rinse was done to remove excess acid from the resin, which can cause poor chromatographic separation. The reagent water volume was optimized from 0.5 to 2.0 mL in 0.5 mL increments. The % recovery decreased with increasing rinse volume. However, there was only an 8% difference between 0.5 (69% Recovery) and 2.0 mL (61% Recovery) for the Total HAA9, and less than 10% difference between 0.5 and 1.0 mL for the individual HAAs, with the exception of DCAA at 30% difference. Although results were better when rinsing with 0.5 mL, a 1.0 mL rinse volume was chosen to provide a separation between the acid loading step and base elution step on the SPE cartridge, and elute more unwanted anions that might negatively affect the chromatography in a real-world drinking water sample. The average % Recoveries resulting from the optimized conditions were as follows: 17±4% for MCAA, 65±14% for MBAA, 58±6% for DCAA, 77±2% for BCAA, 73±3% for DBAA, 74±10% for TCAA, 75±2% for BDCAA, 61±2% for DBCAA, 33±9% for TBAA, and 68±2% for the TOTAL.

Figure 5:
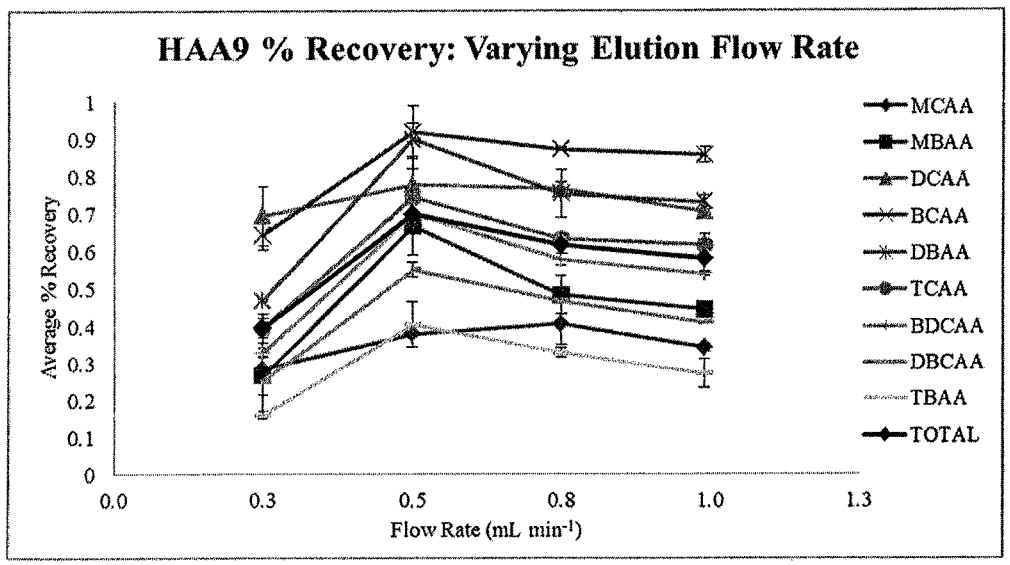
FIG. 5 shows the optimization plot of the elution flow rate for the SIA preconcentration method prior to PCR-IC analysis.

FIG. 5 shows the optimization plot of the elution flow rate, indicating trends in the average percent recovery values for individual HAAs as well as the total amount of HAAs.

Optimization of sample pH was then considered. It appears that at the pH of drinking water, the HAAs are ionized in solution with p$K_a$ values of the HAA9 species ranging from 0.6 for TCAA to 2.9 for MBAA. Thus, a drinking water sample must be acidified to protonate the HAAs for adsorption onto the non-polar stationary phase. To simplify the study, the pH of the HAA standard was adjusted manually by adding concentrated acid drop wise and reading with a pH meter. The acidified standard was loaded onto the SPE cartridge using the automated SIA module followed by analysis using the PCR-IC.

Figure 6:
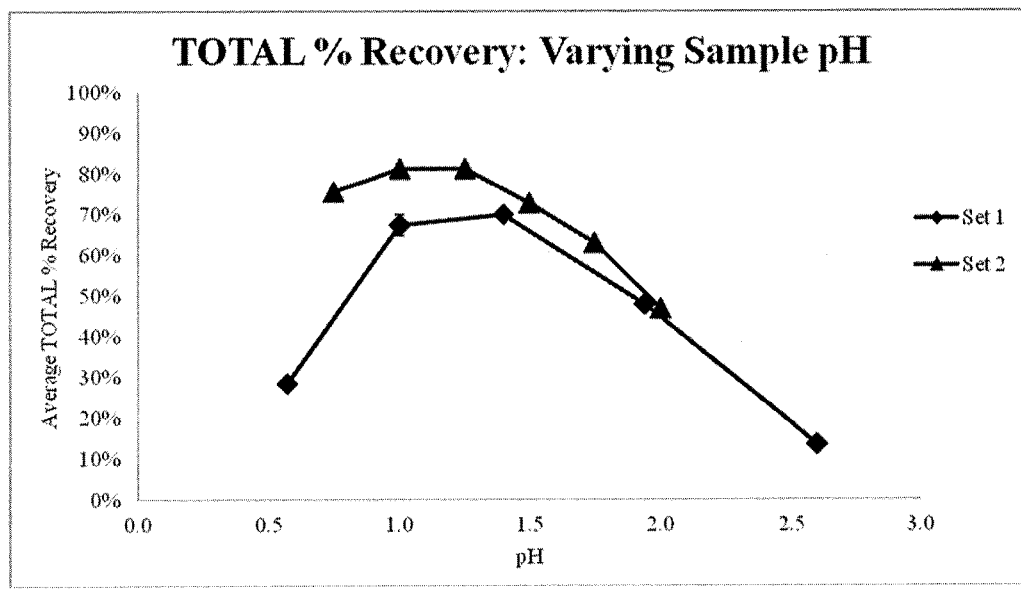
FIG. 6 is an optimization plot of the pH for the sample being loaded for preconcentration of HAA9 using SIA prior to PCR-IC analysis.

A preliminary study was conducted over a pH range 0.5 to 2.5 to narrow the range for optimal preconcentration (FIG. 6, Set 1). At pH values below 0.8, the resolution of the dihalogenated HAAs was greatly affected by unusual peak shapes and poor resolution, similar to effects previously encountered when conditioning the SPE cartridge with sulfuric acid (such as B of FIG. 3). The preliminary results indicated the optimal sample pH is between 1.0 and 1.9 (FIG. 6, Set 1).

The detailed sample pH study was performed over the pH range 0.8 to 2.0 in 0.3 pH unit increments (FIG. 6, Set 2). The optimal % Recovery was obtained in the pH range 1.0 to 1.3 for all HAA9 species except MCAA at pH 0.8 and TBAA at pH 1.8. The Total HAA9% Recovery was 81±1% for both pH 1.0 and 1.3, 5% higher than pH 0.8 and 8% higher than pH 1.5. The average % Recoveries for the individual HAA9 species were: 54±4% for MCAA at pH 1.3, 55±7% for MBAA at pH 1.0, 94±4% for DCAA at pH 1.3, 103±3% for BCAA at pH 1.3, 93±1% for DBAA at pH 1.3, 96±4% for TCAA at pH 1.0, 81±1% for BDCAA at pH 1.0, 67±1% for DBCAA at pH 1.3, 36±4% for TBAA. After establishing the optimal sample pH range, trial and error was used to determine the concentration of sulfuric acid and relative flow rates for the sample and acid lines to acidify the sample to pH 1.0-1.3. The optimal sample flow rate was 2.1 mL min$^{-1}$ and the optimal acid concentration was 1.0 M H$_2$SO$_4$ at a flow rate of 0.6 mL for a total flow of 2.7 min$^{-1}$.

Figure 7:
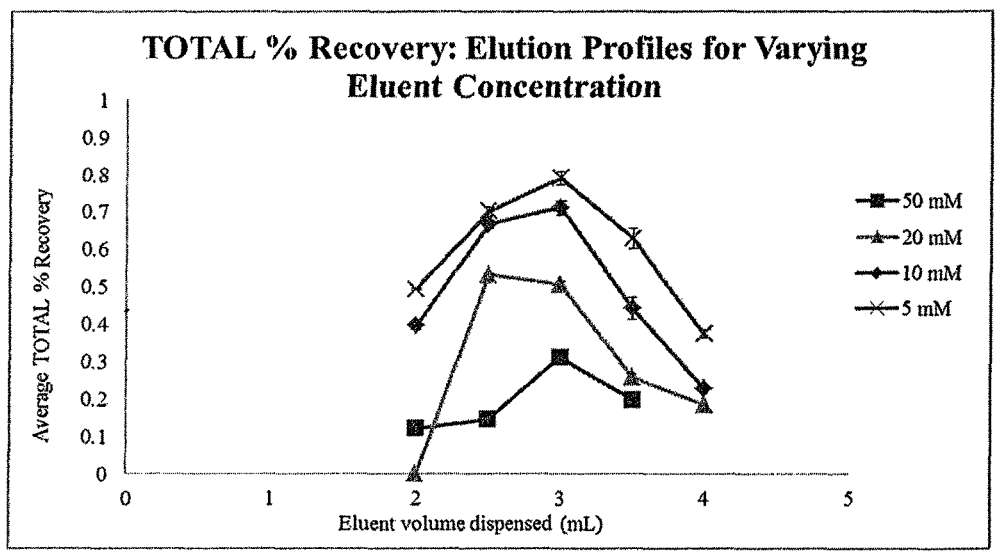
FIG. 7 shows elution profiles for preconcentrations of HAAs with SIA, followed by analysis using PCR-IC.

Work then commenced to optimize eluent concentrations and timing. Such optimization of the NaOH eluent concentration and volume was conducted by varying the concentration from 5 to 50 mM NaOH and elution volume from 2 to 4 mL in 0.5 mL increments. The sample injection valve on the PCR-IC injects a 2-mL aliquot at the tail-end of the eluting volume (e.g. the last 2 mL of the 4 mL eluting volume is injected). The elution study of 5 mM, 10 mM, and 20 mM NaOH were analyzed in triplicate at each elution volume and found that 5 mM and 10 mM produced the overall best % Recovery results for the individual and Total HAA9 species (FIG. 7). The 20 mM NaOH produced rapid decreases in % recovery for the HAA9 species and 50 mM NaOH produced poor chromatographic separation of the mono- and dihalogenated HAA9 species. In addition, 5 mM and 10 mM are advantageous because both NaOH concentrations are similar to the initial PCR-IC gradient separation conditions (2 mM KOH initial concentration). The 10 mM NaOH was ultimately chosen because the chromatographic separation between dihalogenated HAA species was better, even though 5 mM NaOH had slightly higher recoveries.

FIG. 7 shows such elution profiles for preconcentrations of HAAs with average HAA total % Recovery values observed for eluent concentrations of 5, 10, 20, and 50 mM NaOH, (with such variances achieved through varying the eluent volume dispensed through the SPE cartridge).

Experimental Preconcentration Factor Considerations

After completing the method optimizations, the experimental preconcentration factor (PF) for each of the HAAs was determined. A calibration curve was constructed from 25 to 65 µg $L^{-1}$ for each HAA9 species (without preconcentration), and then a check standard of 50 µg $L^{-1}$ each HAA9 species was analyzed in duplicate with and without preconcentration. The preconcentrated HAAs concentrations were calculated using the linear regression trend from the calibration curve, and previous research has shown the linear range for individual HAA9 species includes concentrations up to 912 µg $L^{-1}$. The experimental PF values were determined for the individual HAAs by dividing the reported HAA concentration using preconcentration by the reported HAAs concentration without preconcentration (theoretical PF is 25). The resulting PF values ranged from the lowest for MCAA at 7±0.1 up to the highest for MCAA at 21±1.3 (Table 1), and the average PF for all HAA9 species was 16±1.0. The final % Recovery values were reported as the percent of the experimental PF divided by the theoretical PF (Table 1). With the exception of MCAA, all of the PF values were above 10, which indicates that the method should be able to detect HAAs at concentrations at least an order of magnitude lower than those previously reported.

MDL Studies and Results

The optimized, automated preconcentration SIA-PCR-IC analyzer was used to conduct detailed MDL, accuracy, precision, and linearity studies with IS calibration for individual and Total HAA9 species. Calibration standards were prepared at concentrations from 0.5 to 30 µg $L^{-1}$ for each HAA9, and the IS was manually added to both calibration and check standards at 5 µg $L^{-1}$ 2-BBA. Calibration plots were constructed by plotting the ratio of peak areas for HAAs to the IS peak area, and a linear regression was calculated. A check standard with a concentration of 3 µg $L^{-1}$ HAA9 was analyzed seven consecutive times and concentrations were calculated using the slope and y-intercept of the linear regression line. The absolute error and relative error were calculated based on the reported check standard concentration. Three different approaches were used to determine detection limits for the individual HAAs: the USEPA MDL, traditional MDL, and uncertainty MDL. The USEPA MDL is determined using USEPA recommended guidelines based on the standard deviation of the calculated check standard concentration. The traditional MDL is calculated as three times the standard deviation of noise in a blank analysis, and the Uncertainty MDL is based on the propagation of error of the linear regression line. The accuracy was estimated by mean % recovery, while precision was estimated by % relative standard deviation (% R.S.D.). The dynamic range is defined as the range between the limit of quantitation and limit of linearity, and was determined in a separate study with calibration standards ranging from 10 to 400 µg $L^{-1}$ of each HAA9.

The results of the detailed MDL, accuracy, precision, and linearity studies are presented in Table 1 and 2. All three methods for determining the MDL produced similar results, with values for each species within 2 µg $L^{-1}$ of each other, and all MDL estimates were less 2.5 µg $L^{-1}$ for all HAA9 species. The Uncertainty MDLs were the highest for each analyte, ranging from 1.0 to 2.5 µg $L^{-1}$. The USEPA and Traditional MDL values were excellent and within 0.1 µg $L^{-1}$ of each other for each of the HAA9 species. The USEPA MDL values ranged from 0.3 to 1.0 µg $L^{-1}$ and Traditional MDL values ranged from 0.3 to 0.9 µg $L^{-1}$. When compared to previously reported results obtained using the PCR-IC, these MDL values are almost a factor of 10 lower for each HAA9 species. Results for DCAA improved considerably, which has shown to be beneficial for on-line, remote drinking water analytical procedures, where DCAA is typically the most abundant of the HAAs but gives the poorest response using the nicotinamide fluorescence chemistry.

Mean % recovery values (an estimate of accuracy) are within 100±30%, and % R.S.D. values (an estimate of precision) are all below 10% (Table 2). The ranges for both mean % recovery and % R.S.D. are within the guidelines recommended by the USEPA. Absolute error values were below 0.9 µg $L^{-1}$ and relative error values ranged from 1% for DCAA to 24% for BCAA.

The dynamic range for all of the HAAs was significantly improved compared to previous reports. The limits of quantitation were improved by a factor of 2 to 11, and all such HAA9 limits were decreased to values between 1 and 3 µg $L^{-1}$ (Table 1), demonstrating performance on par with USEPA 552.3. The limits of linearity for the individual HAA9 species ranged between 100 and 400 µg $L^{-1}$, providing a linear response at least 40 µg $L^{-1}$ above the MCL for HAA5 (0.06 mg $L^{-1}$). All of the correlation coefficient values ($r^2$) for the dynamic range study were at or above 0.992, with 5 of the species having $r^2$ equal to 1.000. It should be noted that the maximum values in the dynamic range for BCAA, BDCAA, DBCAA, and TCAA were limited by the maximum fluorescence signal of the fluorescence detector used here. The following two tables provides analytical figures of merit for the individual HAA9 species for the automated SIA-PCR-IC including: Preconcentration (Preconc.) factors; % Recovery (% Rec.) of the preconcentration; Dynamic range; and detailed MDL, accuracy, precision study results.

TABLE 1

| Analyte | Preconc. Factor | Preconc. % Rec. (%) | Dynamic Range (µg $L^{-1}$) | Abs. Error (µg $L^{-1}$) | Rel. Error (%) |
|---|---|---|---|---|---|
| MCAA | 7 ± 0.1 | 29 | 3-100 | 0.2 | 8 |
| MBAA | 21 ± 1.3 | 84 | 2-100 | 0.4 | 14 |
| DCAA | 16 ± 0.6 | 65 | 2-100 | 0.0 | 1 |
| BCAA | 17 ± 0.8 | 68 | 1-100 | 0.7 | 24 |
| DBAA | 19 ± 1.1 | 75 | 1-400 | 0.3 | 10 |
| TCAA | 20 ± 1.2 | 82 | 2-200 | 0.7 | 22 |
| BDCAA | 15 ± 1.0 | 60 | 1-100 | 0.8 | 28 |
| DBCAA | 12 ± 0.9 | 46 | 2-300 | 0.5 | 15 |
| TBAA | 13 ± 1.5 | 53 | 3-400 | 0.4 | 14 |

TABLE 2

| Analyte | MDL (µg $L^{-1}$) USEPA | MDL (µg $L^{-1}$) Trad. | MDL (µg $L^{-1}$) Unc. | Mean % Rec. (%) | % R.S.D. (%) |
|---|---|---|---|---|---|
| MCAA | 1.0 | 0.9 | 1.1 | 108 | 9.6 |
| MBAA | 0.7 | 0.7 | 2.5 | 114 | 6.8 |
| DCAA | 0.7 | 0.7 | 1.0 | 101 | 7.7 |
| BCAA | 0.4 | 0.4 | 0.6 | 124 | 3.4 |
| DBAA | 0.5 | 0.4 | 1.0 | 110 | 4.5 |
| TCAA | 0.6 | 0.5 | 1.0 | 122 | 4.8 |
| BDCAA | 0.3 | 0.3 | 1.1 | 128 | 2.4 |
| DBCAA | 0.6 | 0.6 | 1.1 | 115 | 5.4 |
| TBAA | 0.8 | 0.8 | 1.6 | 114 | 7.6 |

Water Line Testing

Drinking water samples were collected from seven locations throughout Illinois, Tennessee, Georgia, and Arkansas. All of the samples were analyzed in duplicate for HAAs using the SIA-PCR-IC and USEPA 552.3, and analyzed by both methods within 24 hours of each other to reduce any bias due to continued formation in the sampling bottles. IS calibration was used for both methods to determine individual and Total HAA9 concentrations in samples. For the SIA-PCR-IC analysis, IS was quantitatively added to the individual samples by adding 1 mL of the 500 µg L$^{-1}$ 2-BBA stock standard into a 100-mL volumetric flask and diluting to volume with sample, yielding a final concentration of 5 µg L$^{-1}$ of 2-BBA.

An MDL, accuracy, and precision study for USEPA 552.3 is presented in Table 3. The USEPA MDL, mean % recovery, and % R.S.D. values were determined according to USEPA protocol. The MDL values for the HAA9 species ranged from 0.04 µg L$^{-1}$ for DBAA to MCAA at 0.4 µg L$^{-1}$, with excellent mean % recovery and % R.S.D. for the HAAs. The difference between the two methods' respective HAA9 MDL values range between a low of 0.1 µg L$^{-1}$ for BDCAA and a high 0.6 µg L$^{-1}$ for MCAA, MBAA, DCAA and TBAA. In previous reports, the differences between the two methods' MDL values nearly an order of magnitude higher, ranging between 1.4 µg L$^{-1}$ for DBAA and 4.8 µg L$^{-1}$ for DCAA. The following table thus provides MDL, accuracy, and precision values obtained using USEPA Method 552.3.

TABLE 3

| Analyte | MDL (µg L$^{-1}$) | Mean % Rec. (%) | % R.S.D. (%) |
|---|---|---|---|
| MCAA | 0.4 | 92 | 4.9 |
| MBAA | 0.1 | 97 | 0.8 |
| DCAA | 0.1 | 91 | 0.7 |
| BCAA | 0.1 | 91 | 0.6 |
| DBAA | 0.04 | 105 | 0.4 |
| TCAA | 0.1 | 91 | 0.9 |
| BDCAA | 0.2 | 88 | 2.4 |
| DBCAA | 0.2 | 81 | 2.4 |
| TBAA | 0.2 | 85 | 2.7 |

The comparison of the two methods was based on the bias for the individual and Total HAA9 species calculated as the "experimental value−true value" where the "experimental value" is the SIA-PCR-IC concentration and the "true value" is the USEPA 552.3 concentration. The detailed results of the comparison study are presented in Tables 4-7, and include the individual HAAs, Total HAA5 and Total HAA9 concentrations for SIA-PCR-IC and USEPA 552.3 with the calculated bias values. For the SIA-PCR-IC, individual HAAs concentrations ranged from ND (not detected) up to 40.4±0.3 µg L$^{-1}$ for DCAA in Sample C. The Total HAA5 concentrations for SIA-PCR-IC ranged from 1.8±0.3 µg L$^{-1}$ in Sample F up to 67.9±0.9 µg L$^{-1}$ in Sample C; Total HAA9 concentrations ranged from 2.0±0.1 µg L$^{-1}$ in Sample F up to 73.6±0.8 µg L$^{-1}$ in Sample C. For USEPA 552.3, individual concentrations ranged from ND up to 27.8±0.3 µg L$^{-1}$ for DCAA in Sample G. The Total HAA5 concentrations for USEPA 552.3 ranged from 0.2±0.0 µg L$^{-1}$ in Sample F up to 48.7±0.4 µg L$^{-1}$ in Sample G; THAA9 concentrations ranged from 2.9±0.6 µg L$^{-1}$ in Sample F up to 56.0±0.4 µg L$^{-1}$ in Sample G. The bias for the individual analytes ranged from −5.5±0.1 µg L$^{-1}$ for TCAA in Sample A up to 20.2±0.4 µg L$^{-1}$ for DCAA in Sample C. Total HAA5 biases ranged from −9.8±0.4 µg L$^{-1}$ in Sample A up to 21.0±1.9 µg L$^{-1}$ in Sample C. Total HAA9 biases ranged from −13.2±0.5 µg L$^{-1}$ in Sample A up to 20.9±1.9 µg L$^{-1}$ in Sample C.

Figure 8:
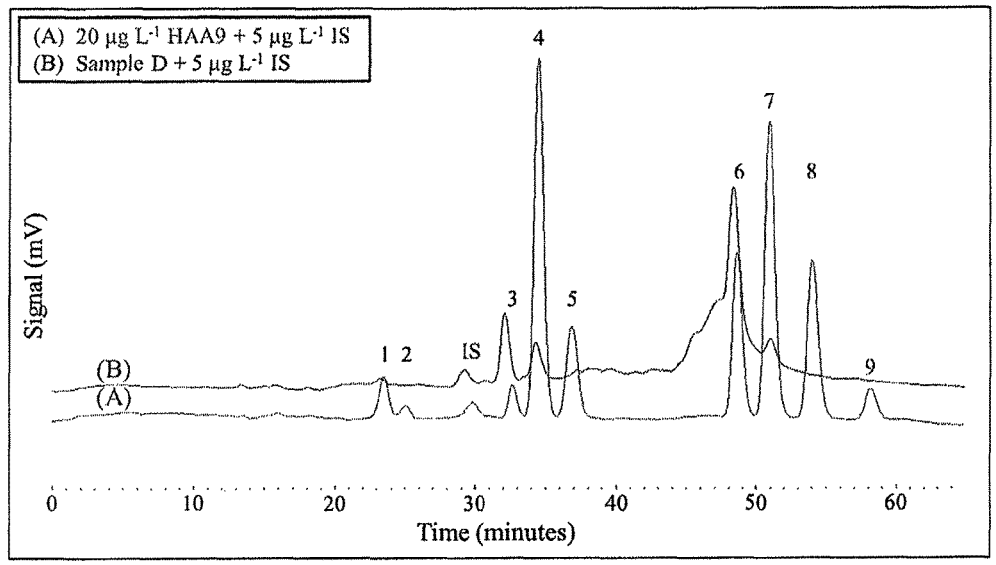
FIG. 8 shows standard and sample chromatograms obtained using the SIA-PCR-IC with nicotinamide fluorescence.

The results of the comparison study demonstrate the effectiveness of the automated SIA-PCR-IC analyzer to determine individual HAAs, Total HAA5, and Total HAA9 concentrations in a variety of drinking water matrices. In the seven samples analyzed, a total of 63 measurements were made on the individual HAA9 species and 89% of these measurements had bias values less than 3 µg L$^{-1}$, with the remaining bias for Total HAA5 and Total HAA9 of the samples largely contributed by DCAA for all of the samples except Sample F. The DCAA bias accounted for the majority of the bias in Samples B, C, D, E, and G. If DCAA is not included, the individual biases ranged from a minimum of −5.5±0.1 µg L$^{-1}$ for TCAA in Sample A, to a maximum of 1.7±0.6 µg L$^{-1}$ for TCAA in Sample C, with an average bias of only −0.2 µg L$^{-1}$ for the individual HAA9 species. FIG. 8 illustrated the analysis using the SIA-PCR-IC of a 20 µg L$^{-1}$ HAA9 standard overlaid with that of Sample D, both containing 5 µg L$^{-1}$ IS. Each of the 10 labeled peaks line up well between the sample and standard with respect to retention time and shape without sample clean up through removal of chloride ions or sulfate ions as needed in previous reports. When integrating peaks 6 and 7, the calculated area of the peaks excluded the large interference baseline shift from ~44 to 54 minutes.

FIG. 8 thus shows such chromatograms obtained using the SIA-PCR-IC with nicotinamide fluorescence. Chromatogram (A) is a 20 µg L$^{-1}$ HAA9 standard with 5 µg L$^{-1}$ IS while (B) is from analysis of Sample D with 5 µg L$^{-1}$ IS. The same legend for HAA identification as in FIG. 3 are present here.

The results of the SIA-PCR-IC are a large improvement over the traditional PCR-IC measurements. Here, as opposed to prior PCR-IC MDL values (which results are nearly an order of magnitude higher than the USEPA method MDL values), only 6 of 63 measurements (9.5%) were less than the MDL or "not detected" by the SIA-PCR-IC analyzer. In essence, the rate of false negatives was greatly decreased, showing that the inventive SIA-PCR-IC was able to report concentrations and speciation trends on par with the USEPA 552.3. The following four tables show concentration and bias values for HAAs detected using SIA Preconcentration with PCR-IC analysis versus the USEPA Method 552.3. For the following Tables 4-7, Bias is the result of subtracting the USEPA value from the PCR-IC value. There was also no "integrate-able" peak for the PCR-IC measures; as a result, the appropriate MDL value used for this calculation. Similarly, since there was no "integrate-able" peak for USEPA 552.3 results, MDL values were also used for such calculations.

TABLE 4

| | Sample A Concentration (µg L$^{-1}$) | | | Sample B Concentration (µg L$^{-1}$) | | |
|---|---|---|---|---|---|---|
| Analyte | PCR-IC | USEPA | Bias | PCR-IC | USEPA | Bias |
| MCAA | 1.0 ± 0.1 | 1.9 ± 0.0 | −0.8 ± 0.1 | 3.0 ± 0.4 | 3.1 ± 0.1 | −0.1 ± 0.4 |
| MBAA | 0.9 ± 0.1 | 0.4 ± 0.0 | 0.5 ± 0.2 | 1.1 ± 0.0 | 0.5 ± 0.2 | 0.6 ± 0.2 |
| DCAA | 10.8 ± 0.4 | 14.7 ± 0.1 | −3.9 ± 0.4 | 21.5 ± 0.3 | 14.2 ± 0.2 | 7.3 ± 0.4 |

TABLE 4-continued

| | Sample A Concentration (µg L$^{-1}$) | | | Sample B Concentration (µg L$^{-1}$) | | |
|---|---|---|---|---|---|---|
| Analyte | PCR-IC | USEPA | Bias | PCR-IC | USEPA | Bias |
| BCAA | 2.0 ± 0.1 | 4.4 ± 0.0 | −2.3 ± 0.1 | 1.3 ± 0.1 | 1.1 ± 0.0 | 0.2 ± 0.1 |
| DBAA | ND | ND | ND | ND | ND | ND |
| TCAA | 11.3 ± 0.1 | 16.8 ± 0.0 | −5.5 ± 0.1 | 26.3 ± 1.0 | 25.3 ± 0.8 | 1.1 ± 1.8 |
| BDCAA | 2.5 ± 0.1 | 4.2 ± 0.2 | −1.7 ± 0.2 | 2.8 ± 0.1 | 1.0 ± 0.0 | 0.9 ± 0.1 |
| DBCAA | 1.4 ± 0.0 | 0.8 ± 0.0 | 0.6 ± 0.0 | ND (0.6) | 0.6 ± 0.0 | $^b$0.0 ± 0.0 |
| TBAA | ND | ND | ND | ND | ND | ND |
| THAA5 | 24.0 ± 0.3 | 33.8 ± 0.2 | −9.8 ± 0.4 | 52.0 ± 2.4 | 43.1 ± 0.5 | 8.9 ± 2.4 |
| THAA9 | 30.0 ± 0.3 | 43.2 ± 0.4 | −13.2 ± 0.5 | 56.1 ± 2.6 | 46.7 ± 0.5 | 9.5 ± 2.7 |

TABLE 5

| | Sample C Concentration (µg L$^{-1}$) | | | Sample D Concentration (µg L$^{-1}$) | | |
|---|---|---|---|---|---|---|
| Analyte | PCR-IC | USEPA | Bias | PCR-IC | USEPA | Bias |
| MCAA | 2.9 ± 0.0 | 2.9 ± 0.0 | 0.0 ± 0.0 | 2.4 ± 0.1 | 2.7 ± 0.1 | −0.3 ± 0.1 |
| MBAA | 0.7 ± 0.0 | 1.6 ± 1.6 | −0.8 ± 1.6 | 0.7 ± 0.0 | 0.4 ± 0.1 | 0.4 ± 0.1 |
| DCAA | 40.4 ± 0.3 | 20.2 ± 0.3 | 20.2 ± 0.4 | 37.0 ± 0.5 | 18.3 ± 0.2 | 18.7 ± 0.5 |
| BCAA | 2.5 ± 0.0 | 2.9 ± 0.1 | −0.4 ± 0.1 | 1.4 ± 0.0 | 1.6 ± 0.0 | −0.2 ± 0.0 |
| DBAA | ND | ND | ND | ND | ND | ND |
| TCAA | 23.8 ± 0.6 | 22.1 ± 0.2 | 1.7 ± 0.6 | 14.2 ± 0.1 | 15.5 ± 0.2 | −1.3 ± 0.2 |
| BDCAA | 3.2 ± 0.1 | 2.4 ± 0.0 | 0.9 ± 0.1 | 1.4 ± 0.0 | 0.5 ± 0.0 | 0.9 ± 0.0 |
| DBCAA | ND (0.6) | 0.6 ± 0.0 | $^b$0.0 ± 0.0 | 1.3 ± 0.0 | 0.6 ± 0.0 | 0.7 ± 0.0 |
| TBAA | ND | ND | ND | ND | ND | ND |
| THAA5 | 67.9 ± 0.9 | 46.8 ± 1.6 | 21.0 ± 1.9 | 54.3 ± 0.5 | 36.9 ± 0.1 | 17.5 ± 0.5 |
| THAA9 | 73.6 ± 0.8 | 52.7 ± 1.7 | 20.9 ± 1.9 | 58.4 ± 0.4 | 39.5 ± 0.1 | 18.9 ± 0.5 |

TABLE 6

| | Sample E Concentration (µg L$^{-1}$) | | | Sample F Concentration (µg L$^{-1}$) | | |
|---|---|---|---|---|---|---|
| Analyte | PCR-IC | USEPA | Bias | PCR-IC | USEPA | Bias |
| MCAA | 1.5 ± 0.2 | 1.9 ± 0.1 | −0.4 ± 0.2 | ND | ND | ND |
| MBAA | 0.7 ± 0.0 | 0.3 ± 0.0 | 0.4 ± 0.0 | ND | ND | ND |
| DCAA | 18.5 ± 1.7 | 9.8 ± 0.6 | 8.8 ± 1.8 | ND (0.7) | 0.2 ± 0.0 | $^b$0.5 ± 0.0 |
| BCAA | 1.0 ± 0.0 | 1.5 ± 0.1 | −0.5 ± 0.1 | 0.5 ± 0.0 | 0.1 ± 0.1 | 0.4 ± 0.1 |
| DBAA | ND | ND | ND | ND | ND | ND |
| TCAA | 13.8 ± 0.6 | 14.8 ± 0.2 | −1.0 ± 0.6 | 0.3 ± 0.7 | ND (0.1) | $^c$0.2 ± 0.2 |
| BDCAA | 2.4 ± 0.1 | 1.2 ± 0.2 | 1.2 ± 0.2 | 0.7 ± 0.1 | ND (0.2) | $^c$0.5 ± 0.1 |
| DBCAA | ND (0.6) | 0.6 ± 0.0 | $^b$−0.1 ± 0.0 | 0.6 ± 0.1 | 1.2 ± 0.1 | −0.6 ± 0.1 |
| TBAA | ND | ND | ND | ND (0.8) | 1.4 ± 0.1 | $^b$−0.6 ± 0.1 |
| THAA5 | 34.5 ± 2.1 | 26.8 ± 0.9 | 7.8 ± 2.3 | 1.8 ± 0.3 | 0.2 ± 0.0 | 1.6 ± 0.3 |
| THAA9 | 37.9 ± 2.3 | 30.1 ± 0.8 | 7.8 ± 2.4 | 2.0 ± 0.1 | 2.9 ± 0.6 | −1.0 ± 0.6 |

TABLE 7

| | Sample G Concentration (µg L$^{-1}$) | | |
|---|---|---|---|
| Analyte | PCR-IC | USEPA | Bias |
| MCAA | 2.8 ± 0.3 | 3.3 ± 0.0 | −0.5 ± 0.3 |
| MBAA | ND (0.7) | 1.0 ± 0.0 | $^b$−0.3 ± 0.0 |
| DCAA | 31.1 ± 2.3 | 27.8 ± 0.3 | 3.3 ± 2.4 |
| BCAA | 3.8 ± 0.2 | 3.9 ± 0.2 | −0.2 ± 0.2 |
| DBAA | ND | ND | ND |
| TCAA | 15.9 ± 1.0 | 16.6 ± 0.2 | −0.7 ± 1.0 |
| BDCAA | 3.1 ± 0.1 | 2.5 ± 0.1 | 0.6 ± 0.1 |
| DBCAA | 0.6 ± 0.0 | 0.8 ± 0.0 | −0.2 ± 0.0 |
| TBAA | ND | ND | ND |
| THAA5 | 49.8 ± 3.6 | 48.7 ± 0.4 | 1.1 ± 3.6 |
| THAA9 | 57.3 ± 3.8 | 56.0 ± 0.4 | 1.3 ± 3.9 |

Thus, the inventive method provides measurement levels (exactness) on par with the USEPA "true value" standards, a significant improvement over prior HAA measurement methods.

On-Line Analysis Using Internal Standard Calibrations

The above-described developments provide the analysis of HAAs in various drinking water matrices using on-line internal standardization with preconcentration. However, these measurements were done in a grab sample format. That is, the SIA-PCR-IC analyzer was first calibrated then an internal standard was added manually to the samples prior to analysis. These studies were done with multiple points of operator handling as well as starting the instrument manually. The grab-sample analysis previously discussed demonstrates the ability of the SIA-PCR-IC to provide comparable results to the USEPA method, but does not demonstrate whether an on-line internal standard addition is reliable and reproducible for remote, on-line addition of the calibration standard.

On-line analysis of HAAs using internal standard requires that the addition of the on-line internal standard to the sample must be reliable and reproducible over the course of multiple, repeated runs in a drinking water system. The first is important because the on-line and remote calibration of the SIA-PCR-IC instrument relies on the internal standard signal that is both reliably added to the drinking water sample and in an automated, reproducible way. This means that the internal standard must be added to each and every sample pulled from the drinking water distribution system without operator contact. Additionally, the internal standard must also be added in the same amounts on each analysis. If it is not, then the HAAs concentration results will not be reliable, and all of this must be done without human intervention. For on-line addition of the internal standard with preconcentration, the internal standard (2-BBA) was mixed into the sulfuric acid solution used to accomplish preconcentration. Thus, the internal standard was added to the sample in an automated and reproducible fashion. The 2-BBA in acidified solution was found to be stable for at least 1 week, and is thus suitable for remote monitoring.

An experiment implementing an on-line, preconcentration with an internal standard was conducted to simulate sampling on-line from a drinking water distribution system. This was done by first collecting 4 L of a water sample from Lebanon, Tenn. The collected water sample was then analyzed using on-line, internal standard (IS) SIA-PCR-IC. For this on-line study, the finished drinking water was sampled in an identical way to a typical on-line monitoring study by placing the sample line of the peristaltic pump on the SIA module into the water sample and starting the automated instrument. Once started, the automated instrument reliably and reproducibly controls the pumping of the sample, pumping of the internal standard, preconcentration of the acidified sample, injection of the sample using an electronically controlled valve, separation of the HAAs species using the high-pressure pump, pumping of the post-column reagents, and detection and integration of the HAAs' signal to report HAAs concentrations. At the end of each run, the instrument restarts for next sample (without operator intervention).

Figure 9:
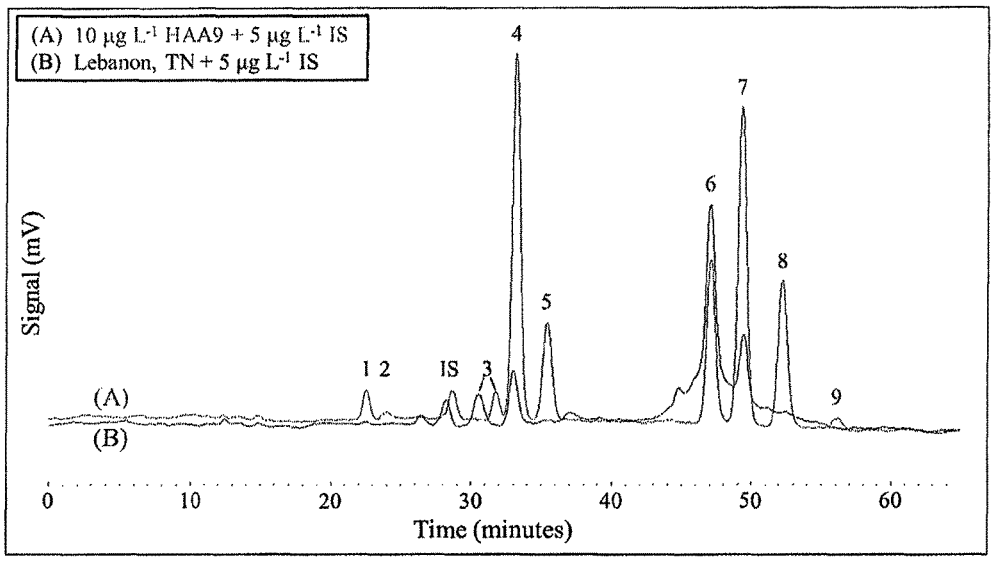
FIG. 9 shows standard and sample chromatograms produced by the SIA-PCR-IC with nicotinamide fluorescence during an on-line 'monitoring' study.
Figure 10:
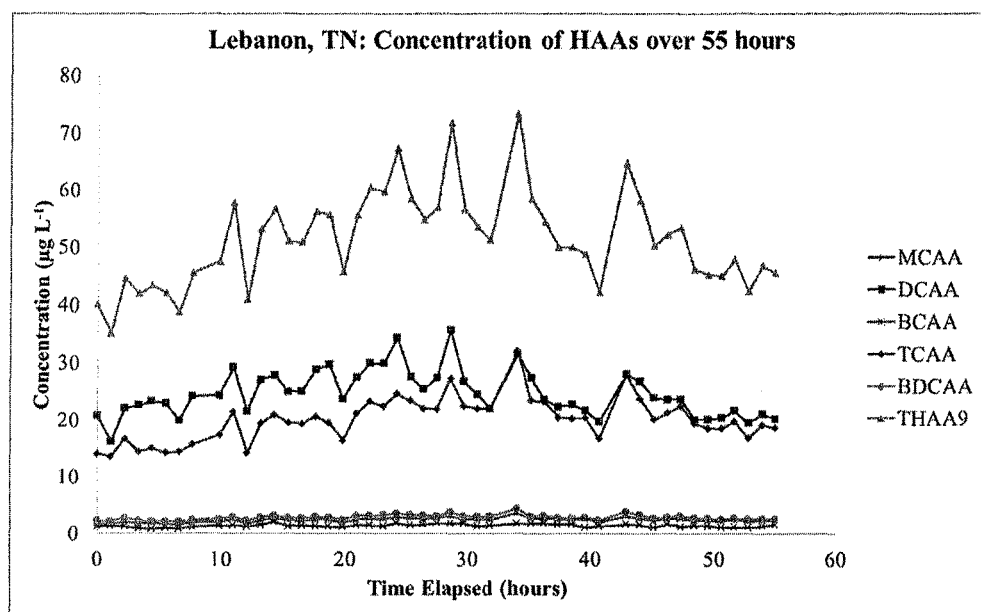
FIG. 10 shows plots of concentrations of HAAs detected in the on-line monitoring study of FIG. 9.

An overlay of 2 chromatograms from the study is illustrated in FIG. 9. Chromatogram (A) is a 10 µg $L^{-1}$ HAA9 standard and Chromatogram (B) is the Lebanon, Tenn. sample, both with automated, on-line addition of 5 µg $L^{-1}$ IS. The retention time for the peaks labeled in the standard chromatogram line up acceptably with those respective peaks detected in the sample; this is important for successful online IS SIA-PCR-IC analysis because the retention time of the detected peak determines the identity of the analyte. A plot of concentration vs. time can be made which shows the on-line IS SIA-PCR-IC analyzer was capable of reliably and reproducibly measuring the concentrations of MCAA, DCAA, BCAA, TCAA, BDCAA, and Total HAA9 (THAA9) in the Lebanon, Tenn. drinking water (FIG. 10). The entire study was carried out over a period of approximately 55 hours. Table 8 shows the variation in the measurements for each of the HAAs, including the range (µg $L^{-1}$) and average (µg $L^{-1}$) detected concentration. The following Table shows variations in HAAs concentrations detected throughout a 55 hour on-line 'monitoring' study of Lebanon, Tenn. drinking water, analyzed by SIA-PCR-IC with nicotinamide fluorescence.

TABLE 8

| Analyte | Range (µg $L^{-1}$) | Average (µg $L^{-1}$) |
| --- | --- | --- |
| MCAA | 0.8-2.0 | 1.4 ± 0.3 |
| DCAA | 16.3-35.7 | 24.7 ± 4.0 |
| BCAA | 1.5-3.6 | 2.4 ± 0.4 |
| TCAA | 13.7-32.0 | 20.1 ± 3.8 |
| BDCAA | 2.1-4.4 | 2.9 ± 0.5 |
| THAA9 | 35.1-73.3 | 51.4 ± 8.3 |

The reproducible nature of adding the internal standard was evaluated by measuring the internal standard peak area over the length of the study. The reproducibility of the on-line addition of internal standard is important because the concentrations of the HAAs are determined based on the peak area of the internal standard. If the peak area of the internal standard changes significantly over the course of the on-line study, then there is a corresponding error on the reported concentrations of the concentrations of HAAs. Table 9 shows the figures of merit for the peak area of the on-line addition of the internal standard. The results show a 15% variation on the average of the signal during on-line introduction of the internal standard. Variations in this range are not uncommon in fluorescence spectrometry, and thus the results and reported error here are acceptable. The following Table thus shows variations in the determined peak area for the internal standard analyzed throughout an on-line study of Lebanon, Tenn. drinking water, analyzed by SIA-PCR-IC with nicotinamide fluorescence.

TABLE 9

| Range (mV · s) | Average (mV · s) | % RSD |
| --- | --- | --- |
| 151-286 | 224-33 | 15% |

FIG. 9 thus shows chromatograms produced by the SIA-PCR-IC with nicotinamide fluorescence during an on-line 'monitoring' study of Lebanon, Tenn. drinking water. Chromatogram (A) is a 10 µg $L^{-1}$ HAA9 standard and Chromatogram (B) is the sample, both with 5 µg $L^{-1}$ IS. FIG. 10 shows plots of concentrations of HAAs detected in the on-line monitoring study of Lebanon, Tenn., drinking water using the SIA-PCR-IC with nicotinamide fluorescence and IS calibration, analyzed over a ~55 hour time period. The same HAA legend as in FIGS. 3 and 8 are used.

Thus, it was determined that a fully-automated, preconcentration procedure for individual and Total HAA9 species was possible, particularly through the utilization of sequential injection analysis prior to analysis by PCR-IC (such as with nicotinamide fluorescence detection procedures). Such a method permits not only a total analysis time of two hours, but the MDL, accuracy, and precision values are nearly an order of magnitude better than PCR-IC without preconcentration and on par with USEPA Method 552.3. Analysis of numerous real-world drinking water samples resulted in acceptable bias values between the SIA-PCR-IC and USEPA 552.3, as well. Basically, then, the inventive SIA-PCR-IC is capable of providing real-time, on-line analysis of the HAA9 species with results equivalent to the USEPA 552.3, but without the need for expert analysts. Hence, the overall system is the most reliable remote system of its kind for water purity analysis.

The preceding examples are set forth to illustrate the principles of the invention, and specific embodiments of operation of the invention. The examples are not intended to limit the scope of the method. Additional embodiments and advantages within the scope of the claimed invention will be apparent to one of ordinary skill in the art.

What we claim is:

1. A fully automated method of analyzing drinking water samples in an on-line procedure and at a remote location along a drinking water supply line, said method including the identification and detection of concentration of haloacetic acid disinfection byproducts therein said drinking water sample, said method comprising:
   a) providing at least one drinking water sample stream that has been disinfected with chlorinated or chloraminated disinfectants;
   b) providing a sequential injection analysis module, wherein said module includes a solid phase extraction component, a chemical reagent pump, and a valve to permit separate delivery of water and chemical reagents to said solid phase extraction component, wherein said reagents include a solid phase extraction component conditioning reagent, an acidic reagent, and a basic reagent, and a separate drinking water sample stream and acid delivery pump to deliver acidified drinking water samples to said solid phase extraction component;
   c) providing a separate PCR-IC instrument including at least one ion exchange column, and a fluorescence detector;
   d) conditioning said solid phase extraction component through introduction therein with said solid phase extraction component conditioning reagent;
   e) feeding said drinking water sample stream through said drinking water sample stream delivery pump into said solid phase extraction component with said acidic reagent from said chemical reagent pump and through said valve, thereby removing at least some of the haloacetic acids from said drinking water stream and forming an acidified preconcentrate formulation including at least one haloacetic acid bound to said solid phase extraction component, wherein said acidic reagent produces a pH in a range from about 0.8 to 2;
   f) feeding said basic reagent through said solid phase extraction component to elute said acidified preconcentrate formulation of step "e" from said solid phase extraction component;
   g) feeding the eluted preconcentrate formulation of step "f" through said PCR-IC instrument, including through said anion exchange column to provide separated haloacetic acid species streams;
   h) mixing said separated haloacetic species streams from step "g" with a dilute base and a fluorescing compound to form separate fluorescing haloacetic acid species streams therein; and
   i) transporting said separate fluorescing haloacetic acid species streams of step "h" to said fluorescence detector to determine the concentration of total haloacetic acids within all such fluorescing haloacetic acid species streams through fluorescence detection.

2. An automated, on-line two-component analytical instrument including:
   a sequential injection analytical module for preconcentrating haloacetic acids from a liquid sample, said module having two separate pumps, a multi-port valve, an acid feeding source, a basic reagent feeding source, a water sample source, and a solid phase extraction device, wherein said valve is configured to deliver alternating streams of acid and water from each pump to said solid phase extraction device, wherein the acid fed by the acid feeding source produces a pH in a range from about 0.8 to 2; and
   a separate PCR-IC device, wherein said PCR-IC device receives said basic reagent and includes an anion exchange column for separating said at least one haloacetic acid into separate species, and a fluorescence detector.

3. The method of claim 1, wherein the basic reagent in step "f" and step "g" are the same.

4. The method of claim 1, further comprising introducing said basic reagent into said anion exchange column at a first rate of flow, maintaining said first rate of flow for a first period of time, and increasing said basic reagent flow into said anion exchange column to a second rate of flow and maintaining said second rate of flow for a second period of time.

5. The method of claim 1, wherein the pH range is between about 1.0 to 1.3.

6. The instrument of claim 2, wherein the pH range is between about 1.0 to 1.3.

* * * * *